US010588922B2

United States Patent
Tauzin

(10) Patent No.: US 10,588,922 B2
(45) Date of Patent: Mar. 17, 2020

(54) METHOD FOR PREPARING AN INJECTABLE CROSS-LINKED HYDROGEL, HYDROGEL OBTAINED; AND USE OF THE OBTAINED HYDROGEL

(71) Applicant: KYLANE LABORATOIRES SA, Plan-les-Ouates (CH)

(72) Inventor: Benedicte Vincente Tauzin, Bogeve (FR)

(73) Assignee: KYLANE LABORATOIRES SA, Plan-les-Ouates (CH)

( * ) Notice: Subject to any disclaimer, the term of this patent is extended or adjusted under 35 U.S.C. 154(b) by 0 days.

(21) Appl. No.: 15/579,216

(22) PCT Filed: Jun. 15, 2016

(86) PCT No.: PCT/FR2016/000096
§ 371 (c)(1),
(2) Date: Dec. 4, 2017

(87) PCT Pub. No.: WO2016/207496
PCT Pub. Date: Dec. 29, 2016

(65) Prior Publication Data
US 2018/0177819 A1  Jun. 28, 2018

(30) Foreign Application Priority Data
Jun. 24, 2015 (FR) .................................... 15 01323

(51) Int. Cl.
| | |
|---|---|
| *A61K 31/728* | (2006.01) |
| *A61K 8/04* | (2006.01) |
| *A61K 8/73* | (2006.01) |
| *A61K 9/06* | (2006.01) |
| *A61Q 19/08* | (2006.01) |
| *C08J 3/075* | (2006.01) |
| *A61K 47/36* | (2006.01) |
| *A61K 8/33* | (2006.01) |
| *C08J 3/24* | (2006.01) |

(52) U.S. Cl.
CPC ............ *A61K 31/728* (2013.01); *A61K 8/042* (2013.01); *A61K 8/33* (2013.01); *A61K 8/735* (2013.01); *A61K 9/06* (2013.01); *A61K 47/36* (2013.01); *A61Q 19/08* (2013.01); *C08J 3/075* (2013.01); *C08J 3/24* (2013.01); *A61K 2800/91* (2013.01); *C08J 2305/08* (2013.01)

(58) Field of Classification Search
CPC ...... A61K 31/728; A61K 8/042; A61K 8/735; A61K 9/06; A61K 2800/91; A61Q 19/08

USPC .......................................................... 514/54
See application file for complete search history.

(56) References Cited

U.S. PATENT DOCUMENTS

| 7,741,476 B2 | 6/2010 | Lebreton |
|---|---|---|
| 8,052,990 B2 | 11/2011 | Hermitte et al. |
| 2009/0169615 A1 | 7/2009 | Pinsky |
| 2010/0303873 A1 | 12/2010 | Piron et al. |
| 2012/0108537 A1* | 5/2012 | Bourdon ................ A61K 8/042 514/54 |
| 2016/0106707 A1 | 4/2016 | Marchal et al. |
| 2018/0318335 A1 | 11/2018 | Tauzin |

FOREIGN PATENT DOCUMENTS

| EP | 0 480 189 | 4/1992 |
|---|---|---|
| EP | 0 499 164 | 8/1992 |
| WO | WO 94/25078 | 11/1994 |
| WO | WO 97/04012 | 2/1997 |
| WO | WO 02/39977 | 5/2002 |
| WO | WO 2004/092222 | 10/2004 |
| WO | WO 2005/085329 | 9/2005 |
| WO | WO 2009/071697 | 6/2009 |
| WO | WO 2010/015900 | 2/2010 |
| WO | WO 2014/173941 | 10/2014 |
| WO | WO 2014/198406 | 12/2014 |

OTHER PUBLICATIONS

Written Opinion in International Application No. PCT/FR2016/000096, dated Aug. 23, 2016, pp. 1-7.
Farkas, J. P. et al. "The Science and Theory behind Facial Aging" *PRS GO*, Apr. 5, 2013, pp. 1-8.
Sundaram, H. et al. "Global Aesthetics Consensus: Hyaluronic Acid Fillers and Botulinum Toxin Type A—Recommendations for Combined Treatment and Optimizing Outcomes in Diverse Patient Populations" *Plastic and Reconstructive Surgery*, May 2016, pp. 1410-1423, vol. 137, No. 5.
Written Opinion in International Application No. PCT/FR2016/000151, dated Dec. 14, 2016, pp. 1-4.

* cited by examiner

*Primary Examiner* — Yih-Horng Shiao
(74) *Attorney, Agent, or Firm* — Saliwanchik, Lloyd & Eisenschenk

(57) ABSTRACT

The present invention relates to: a novel method for preparing an injectable cross-linked hydrogel containing hyaluronic acid, or one of the salts thereof, a hydrogel obtained according to said preparation method, and use of the hydrogel obtained according to said preparation method in the fields of aesthetics and medicine.

16 Claims, No Drawings

METHOD FOR PREPARING AN INJECTABLE CROSS-LINKED HYDROGEL, HYDROGEL OBTAINED; AND USE OF THE OBTAINED HYDROGEL

CROSS-REFERENCE TO RELATED APPLICATION

This application is the U.S. national stage application of International Patent Application No. PCT/FR2016/000096, filed Jun. 15, 2016.

The subjects of the present invention are:
a method for preparing an injectable hydrogel of cross-linked hyaluronic acid, or one of the salts thereof, and optionally of other biocompatible polymers;
a hydrogel obtained with said preparation method;
use of the hydrogel obtained with said preparation method in the cosmetic and medical fields.

Hyaluronic acid is a polysaccharide formed by the repeating of a disaccharide unit composed of D-glucuronic acid and N-acetylglucosamine. It has a linear structure without any specificity for species. Hyaluronic acid is largely distributed in human and animal living organisms in which it performs numerous biological functions such as controlling the rate of hydration for example or maintaining the viscoelasticity of fluids or tissues. It is particularly found in high concentration in synovial fluid, the vitreous body of the eye and in the dermis. A human being weighing 70 kg has about 15 g of hyaluronic acid of which one half is contained in the skin, and this amount decreases with ageing.

Hydrogels of hyaluronic acid have been known and used in wide cosmetic and medical fields for many years. In particular, these gels are frequently injected:
into the eyes during ophthalmic surgery to maintain the intra-ocular space and protect eye tissue;
into joints in cases of arthritis, to supplement deficient synovial fluid and temporarily to restore the chondro-protective properties of said biological fluid;
into or under the skin to fill in wrinkles or increase the volume of some regions of the face or body.

Hyaluronic acid has a short half-life in living organisms (less than 1 week).

In numerous cosmetic or medical applications, it is injected into patients in its native form i.e. it is not cross-linked and/or chemically modified.

For other applications, it is administered to patients in a form stabilized by crosslinking. Crosslinking allows a considerable increase in the lifetime (also called remanence) of hyaluronic acid in vivo, but it also allows modifications of its mechanical and rheological properties in particular by making it more elastic, thereby increasing its capacity to create volume once injected into the desired tissues. Therefore, through this modification via crosslinking, a crosslinked hyaluronic acid hydrogel has the capacity for example to fill in wrinkles over a period of several months.

Having regard to the key role played by crosslinked hyaluronic acid in the cosmetic and medical fields, persons skilled in the art are constantly seeking to improve this molecule by imparting thereto better biomechanical and/or remanence characteristics, whilst preserving a very high level of safety.

The present invention precisely sets out to propose a novel method for preparing an injectable hydrogel of cross-linked hyaluronic acid or one of the salts thereof, and optionally other biocompatible polymers and/or any other ingredient able to contribute a benefit to the product; a method which notably allows:

a significant increase in the elasticity and remanence of the hydrogel obtained, and hence the clinical performance thereof;
a reduction in the amount of crosslinking agent, a molecule that is not devoid of some toxicity, to be added to the reaction mixture when crosslinking the hyaluronic acid, to improve the safety profile of the injectable hydrogel obtained;
limiting of the presence of oxygen-derived free radicals when preparing the product but also during storage thereof (during its use-by period) and when used in a patient, to reduce the deleterious effects induced by these undesirable entities on hyaluronic acid but also on the treated region of the patient.

Therefore, in a first of its aspects, the present invention concerns a method for preparing an injectable hydrogel of crosslinked hyaluronic acid, or one of the salts thereof, and optionally of other biocompatible polymers, comprising at least the following steps:
preparing a hydrogel integrating at least one crosslinking step of the hyaluronic acid in an aqueous solution;
purifying the hydrogel;
packaging the hydrogel in syringes or bottles;
sterilization,
by performing mandatorily at least the crosslinking step of hyaluronic acid in an inert atmosphere and mandatorily at least one extraction step of the oxygen contained in the hydrogel; the extraction step being performed after the crosslinking step of the hyaluronic acid in an inert atmosphere and before and/or at the time of the hydrogel packaging step; the extraction step consisting of performing at least one extraction cycle in a suitable container, characterized by the following successive phases:
placing the container containing the hydrogel under a vacuum at a pressure p lower than atmospheric pressure for a time t;
breaking the vacuum after time t by adding an adapted quantity of a gas other than oxygen.

According to one embodiment of the invention, the inert atmosphere used consists of one or more medical grade gases.

According to one embodiment, the constituent gas(es) of the inert atmosphere used to substitute oxygen at the crosslinking reaction step are selected from among hydrogen, helium, nitrogen and argon.

According to one embodiment of the invention, the pressure of the inert atmosphere is equal to or higher than atmospheric pressure. This pressure can be fixed or it may vary over time.

According to the invention, this preparation method also allows efficient extraction of the oxygen contained in the hydrogel. This extraction step is performed after the crosslinking step of the hyaluronic acid and before and/or at the time of the hydrogel packaging step. It is to be noted that according to the invention, the crosslinking of the hyaluronic acid is conducted in an inert atmosphere and that, after crosslinking, a purification step (advantageously via dialysis) and one or more homogenization steps are to be carried out; these steps most generally being performed in air. It is therefore important to specify that it is not because the crosslinking step is performed in an inert atmosphere that there is no re-addition of oxygen to the hydrogel at a step following after crosslinking, hence the advantage of extracting this oxygen efficiently before or at the time of packaging the gel.

The performing of one or more extraction cycles, involving application of a vacuum at an adapted pressure, followed by breaking this vacuum with a suitable gas not containing oxygen (and hence no air) allows most of the oxygen contained in the product to be removed. When placed under a vacuum, advantageously performed dynamically, the gas molecules contained in the hydrogel and therefore in particular the oxygen molecules are carried away by the applied vacuum. By breaking the vacuum with a gas not containing oxygen, it is possible not to reintegrate oxygen into the product.

The performing of several extraction cycles therefore allows the removal of an ever-increasing amount of oxygen, accumulated over these extraction cycles.

It is to be noted that the progress of the oxygen extraction operation, advantageously performed in a container of vacuum chamber type, can be visually observed if the container containing the hydrogel is transparent. When the product is placed under a vacuum, the hydrogel is seen to expand. By expansion of the hydrogel is meant the fact that its volume increases inside the container. When the vacuum is broken, the hydrogel immediately returns to a volume close to its initial volume, thereby taking part in expelling the residual oxygen contained in the gel. By multiplying the extraction cycles, it is ascertained that the expansion of the hydrogel in the container becomes smaller throughout the cycles, a sign that there is less and less gas and hence oxygen in the gel.

To break the vacuum, a light gas of small size such as helium is advantageously chosen to facilitate the oxygen extraction procedure.

In addition, having regard to the injectable nature of the product, a medical grade gas is advantageously chosen to ensure full safety of the manufactured product.

It is important to point out that the oxygen extraction step of the preparation method of the invention brings major advantages for the manufacturer compared with the so-called "degassing" technique of the prior art. Degassing is intended to remove small air bubbles contained in the gel, thereby providing a better appreciated visual appearance for end users (practitioners and patients), but it does not remove most of the oxygen contained in the product. Compared with this prior art degassing technique, the proposed solution allows:
  also the removal of air bubbles contained in the gel to improve the visual appearance thereof;
  efficient extraction of the oxygen contained in the gel throughout the extraction cycles;
  considerable savings in time since the oxygen extraction cycles to be applied can be of very short duration, contrary to degassing in the prior art which entailed a waiting time for gradual escape of air from the gel when placed under a vacuum (this, in addition to the lengthy time needed for performing thereof, also inducing dehydration of the hydrogel).

It is also important to point out that it is within the reach of persons skilled in the art, as a function of the specific characteristics of its formulation (hyaluronic acid concentration, crosslinking rate, presence of other compounds, . . . ), to select the appropriate conditions to extract oxygen from the product and to obtain optimization thereof (pressure p and vacuum time t, quantity of gas to break the vacuum, number of extraction cycles to be performed, . . . ).

According to one embodiment of the invention, a single step to extract the oxygen contained in the hydrogel is performed throughout the production of the injectable product.

According to another embodiment of the invention, between 2 and 4 steps to extract the oxygen contained in the hydrogel are performed throughout the production of the injectable product.

According to one embodiment of the invention, a step to extract the oxygen contained in the hydrogel is performed before or at the time of packaging this hydrogel in syringes or bottles.

According to one embodiment of the invention, a step to extract the oxygen contained in the hydrogel is performed before adding an ingredient to the gel, e.g. an active ingredient which may become oxidized by the oxygen contained in this gel.

According to one particular embodiment of the invention, a step (performed as previously described) to extract the oxygen contained in the reaction mixture is also performed before the crosslinking step of the hyaluronic acid in an inert atmosphere. This additional step allows the removal of any oxygen which may be present in the reaction mixture before crosslinking, in particular if the steps preceding crosslinking (e.g. preparation of the aqueous solution of hyaluronic acid) were performed in air i.e. in the absence of an inert atmosphere.

According to one embodiment of the invention, the oxygen extraction step is performed by applying between 1 and 50 extraction cycles, characterized by applying a vacuum and breaking this vacuum using a gas other than oxygen. Advantageously, the number of applied cycles is between 2 and 10, preferably between 3 and 6 throughout the oxygen extraction step.

According to one embodiment of the invention, the sterilization of the product is obtained under heat, preferably moist heat.

According to another embodiment of the invention, sterilization is performed using an aseptic method.

According to one preferred embodiment of the invention, the hydrogel is packaged in syringes.

According to one embodiment of the invention, the gas used to break the vacuum when extracting oxygen is a gas lighter than air.

According to one embodiment of the invention, the gas used is an inert gas.

According to one embodiment of the invention, the gas used is a medical grade gas.

According to one embodiment of the invention, the gas used is selected from among hydrogen, helium, nitrogen and argon. Advantageously, the gas used is nitrogen or helium.

According to one embodiment of the invention, the gas used is a mixture of different gases other than oxygen.

According to one preferred embodiment of the invention, the placing of the hydrogel under a vacuum is performed dynamically (the system creating the vacuum, advantageously a vacuum pump, is permanently connected to the container containing the hydrogel to maintain the desired pressure thereof) rather than statically (the container containing the hydrogel is isolated from the system creating the vacuum once the pressure has reached the desired value).

According to one preferred embodiment of the invention, the pressure p applied when creating the vacuum is lower than 100 mbar, advantageously lower than 50 mbar.

According to the invention, the oxygen extraction step is performed in a suitable container. This container may be a vacuum chamber for example or a desiccator having a valve allowing the chamber to be sealed or the vacuum to be broken. Vacuum application is advantageously ensured using a vacuum pump.

According to one embodiment of the invention, the time t of vacuum application for an extraction cycle is between 1 minute and 60 minutes, preferably between 5 minutes and 25 minutes.

By crosslinking step of the hyaluronic acid is meant the step allowing the bridging together of hyaluronic acid chains via covalent bonds. In general, the hyaluronic acid crosslinking step starts when the crosslinker is placed in contact with the hyaluronic acid and then homogenized in the reaction mixture, and terminates when the person skilled in the art considers that the kinetics of the bridging reaction of the hyaluronic acid chains has reached negligible level.

In the present invention, as previously described, it is mandatory that the crosslinking step is performed in an inert atmosphere.

The preparation of the crosslinked hyaluronic acid hydrogel is preferably performed in accordance with the methods described in the prior art.

The applications WO 97/04012, WO 2004/09222 and WO 2009/071697 can be cited for example for the manufacture of a hydrogel containing crosslinked hyaluronic acid.

One advantageous method of the invention to manufacture a crosslinked hyaluronic acid gel comprises at least the following steps:
  preparing an aqueous solution of hyaluronic acid in an inert atmosphere;
  crosslinking the hyaluronic acid in an inert atmosphere;
  neutralizing the gel obtained to a pH of about 7.0, and removing the crosslinker by purification e.g. via dialysis in a physiological saline solution;
  optionally extracting oxygen with the previously described method;
  optionally adding additional molecules such as vitamins and/or an active ingredient for example;
  homogenizing the gel;
  extracting oxygen with the previously described method;
  packaging in bottles in syringes;
  sterilization.

Another advantageous method according to the invention to manufacture a crosslinked hyaluronic acid gel comprises at least the following steps:
  preparing an aqueous solution of hyaluronic acid;
  extracting oxygen with the previous described method;
  crosslinking the hyaluronic acid in an inert atmosphere;
  neutralizing the gel obtained to a pH of about 7.0, and removing the crosslinker by purification, e.g. via dialysis in a physiological saline solution;
  optionally extracting oxygen with the previously described method;
  optionally adding additional molecules such as vitamins and/or an active ingredient for example;
  homogenizing the gel;
  extracting oxygen with the previously described method;
  packaging in bottles or syringes;
  sterilization.

With the method of the invention, it is possible mandatorily to perform at least the crosslinking step in an inert atmosphere, but also to extract the oxygen contained in the hydrogel most efficiently before and/or at the time of packaging thereof in bottles or syringes.

Most surprisingly and highly advantageously, as illustrated in the examples, the application of the method of the invention allows a significant improvement in the properties of the hydrogel obtained with this method. The following are ascertained:

a significant improvement in the mechanical/rheological properties of the hydrogel, and in particular the elasticity thereof (increase in the elastic modulus G');
  possible reduction in the amount of crosslinker used (a molecule having a certain degree of toxicity) to crosslink the hyaluronic acid, with a view to improving the safety level of the injectable hydrogel obtained;
  significant improvement in the resistance to degradation of the hydrogel;
  better stability of the hydrogel over time.

It is important to point out that the method of the invention has a strong, direct impact on the structure of the hydrogel at the crucial crosslinking step, but also at other steps such as sterilization. The method of the invention therefore imparts considerable benefit to the product obtained with the invention. First, it allows a product to be obtained having better performance but also a safer product, this being of major importance to target even greater tolerance of the numerous treatments using crosslinked hyaluronic acid.

It is thus observed that the product obtained with the invention has better volume-creating capacity (due to its stronger elasticity) and over the longer term (due to its greater capacity to resist degradation but also due to its better stability), hence improved clinical efficacy in the cosmetic and medical fields. The method of the invention also provides the possibility of reducing the amount of crosslinker used (chemical agent not devoid of some toxicity) for one same targeted effective crosslinking rate, thereby allowing an improvement in the safety profile of the injectable product obtained.

In a second of its aspects, the present invention concerns an injectable hydrogel of crosslinked hyaluronic acid obtained with the preparation method described above. This hydrogel may also contain other biocompatible polymers and any other ingredient able to contribute a benefit to the injectable product. This hydrogel is characterized by improved mechanical/rheological and remanence properties compared with a prior art product that has not been subjected to the preparation method of the invention. The hydrogel of the invention has stronger elasticity and greater resistance to degradation (through in vivo degradation factors such as degradation by thermal hydrolysis, radical degradation and enzymatic degradation), to target better clinical performance of the injected product.

The injectable hydrogel of the invention is also crosslinked more efficiently, thereby allowing the use of less crosslinking agent (molecule having some toxicity) to bridge the hyaluronic acid chains in equivalent manner to a prior art gel, thereby reinforcing the safety profile of the product obtained. This essential characteristic of the product of the invention allows the targeting of better tolerance of injectable treatments with crosslinked hyaluronic acid, for example by reducing side effects over the short and/or longer term. It is also important to note that the better controlling/efficacy of crosslinking can allow limiting of the onset hyaluronic acid molecules of low molecular weight in the mixture (in particular, under basic or acid conditions and at higher temperature as is the case when crosslinking); these entities being described in the literature as being pro-inflammatory and hence generators of adverse effects.

The injectable hydrogel of the invention is also more stable during storage i.e. throughout its use-by period. This therefore allows better preservation of the mechanical/rheological properties of the gel (for example, the elastic modulus G' is less deteriorated over time—a parameter that is seen to decrease less over time), but this also allows limiting of the onset of hyaluronic acid molecules of low molecular weight (previously described) over time. This can enable manufacturers to extend the use-by period of the product. Without wishing to be bound by any explanation, this advantage is probably due to the fact that the method of the invention allows very extensive limiting of the amount of oxygen in the hydrogel (oxygen free radicals having a deleterious effect on hyaluronic acid by breaking the chains thereof), but also due to the fact that the method of the invention allows the preparation of a product having a more "robust" structure (as demonstrated by the fact that it has better elasticity and better resistance to degradation).

In addition, the extraction of oxygen according to the invention, as a result of the efficacy thereof, allows reinforced safety for a patient compared with prior art products. The use of the hydrogel of the invention strongly limits the entry of oxygen into the tissues (induced by injection of a hydrogel containing oxygen) thereby contributing to a reduction in the creation of free radicals at the injected region (oxidative stress of the body) and being of benefit for the gel (lesser degradation thereof) but also for the surrounding tissues which are therefore less attacked by free radicals (by contributing towards limiting the inflammatory action that systematically accompanies any type of injection).

According to the invention, the hydrogel contains hyaluronic acid or one of the salts thereof, in particular salts that are physiologically acceptable such as sodium, calcium, zinc, potassium salts, advantageously sodium salt. The hyaluronic acid may be of animal origin or obtained by bacterial fermentation. It may have a molecular weight of a few Daltons to several million Daltons, advantageously about 0.1 to 4 million Daltons.

In one aspect of the invention, the hydrogel may be based on a derivative of hyaluronic acid i.e. a molecule obtained by modifying the hyaluronic acid molecule via chemical or any other route.

In one aspect of the invention, the total concentration of hyaluronic acid or one of the salts thereof in the hydrogel is between 0.01 and 50 mg/ml, preferably between 1 and 35 mg/ml, advantageously between 8 and 30 mg/ml.

In one aspect of the invention, the hydrogel is preferably crosslinked using methods described in the prior art.

The crosslinking agent(s) involved in crosslinking may be the same or different. They are generally bi- or poly-functional crosslinkers of different types and can be selected for example from among divinylsulfone, bi- or poly-functional epoxies, carbodiimides and formaldehyde. Preferably agents are selected from the family of bi- or poly-functional epoxies and in particular 1,4-butanedioldiglycidylether (BDDE), diepoxy-octane or 1,2-bis-(2,3-epoxypropyl)-2,3-ethylene. Particular preference is given to the use of BDDE.

Crosslinking temperatures are generally between about 15° C. and 60° C.

Crosslinking times are generally a few hours, advantageously more than 1 h and up to about 48 h.

In one aspect of the invention, the hydrogel of the invention contains one or more active substances of natural or synthetic origin whether or not having pharmacological action, for example antioxidants, anti-inflammatories, antiseptics, antibacterial agents, antifungal agents, anticancer agents, local anaesthetics, proteins, hormones, alone or in combination. These active substances are either dispersed in the hydrogel or grafted onto one or more of the polymers of the hydrogel, or contained/encapsulated in another material itself dispersed in the hydrogel. In this latter case, mention can be made, for example, of encapsulation of an active substance such as an anti-inflammatory in microspheres of a polymer derived from polylactic acid or poly-ε-caprolactone.

In one aspect of the invention, the hydrogel of the invention contains lidocaine dispersed in the crosslinked matrix thereof.

In one aspect of the invention, the hydrogel of the invention contains one or more compounds of biological origin such as cells, enriched platelets, genes, DNA fragments or growth factors. These compounds are preferably dispersed in the hydrogel, but they may also be grafted onto one or more polymers of the hydrogel or contained/encapsulated in another material itself dispersed in the hydrogel.

In one aspect of the invention, the hydrogel of the invention contains polymers that are dispersed in the crosslinked matrix of the hydrogel. For example, mention can be made of the polymers in the polysaccharide family, polyesters, polyanhydrides, polyphosphazenes, poly-ε-caprolactones, polylactic acids and derivatives thereof, polyvinyl acids, polyacrylamides, N-vinylpyrrolidone, acrylic polymers and biologically acceptable derivatives.

In one aspect of the invention, the hydrogel of the invention contains mineral substances that are dispersed in the crosslinked matrix of the hydrogel. Mention can be made of hydroxyapatite for example or tricalcium phosphates such as β tricalcium phosphate.

In a third of its aspects, the present invention concerns the use in Man or animal of the injectable hydrogel obtained with said preparation method, in the cosmetic and medical fields.

The injectable hydrogel of the invention is notably used to:
fill in volumes;
generate spaces in some tissues, thereby promoting optimal functioning thereof;
replace physiological liquids or deficient tissues;
stimulate or promote tissue regeneration;
hydrate and protect tissues;
deliver substances able to provide the body with a benefit and in particular active and/or biological substances.

For example, uses of the hydrogel can be cited in the following cases:
formulation of an intra-dermal or subcutaneous injectable composition to improve skin quality or to fill in wrinkles or restore volumes of the face (cheekbones, chin, lips, nose, . . . ) or body;
formulation of an injectable composition for dental use, for example to fill in periodontal pockets and/or stimulate regeneration of tissues around teeth;
formulation of an intra-ocular injectable composition, in particular for applications during surgery of the cataract, of glaucoma, farsightedness or of the vitreous body;
formulation of intra-articular injectable compositions for applications in orthopaedics or rheumatology, in particular for visco-supplementation of deficient synovial fluid to treat arthritis, but also for bone reconstruction or regeneration of cartilage;
formulation of an injectable composition in urology for applications to treat urinary or faecal incontinence;
formulation of an injectable composition to be used in medicine or general surgery for the treatment of fibrosis or to improve healing of wounds;
formulation of an injectable pharmaceutical composition allowing the delayed and/or controlled release of active and/or biological substances for different medical applications.

EXAMPLES

The invention will now be illustrated in nonlimiting manner with the following examples.

The sodium hyaluronate (NaHA) and all other compounds used in the examples have a high level of purity.

The rheological properties of the gels (measurement of the elastic modulus G') were measured at 25° C. using a controlled stress rheometer (TA AR2000) with cone/plate geometry of 4 cm-2°.

Example 1: Preparation of a Crosslinked NaHA Gel According to the Invention

A laboratory mixer, under an inert atmosphere composed of 100% helium gas at a pressure of 1.4 bar and at ambient temperature, was charged with 24 g of 0.25 N aqueous NaOH solution, followed by 2.5 g of a sodium hyaluronate powder (NaHA) having a molecular weight of about 1.8 MDa and moisture content of 7.8%. Hydration of the powder lasted 1 h30, with regular mechanical homogenization. 1.3 g of 1,4-butanedioldiglycidylether (BDDE) solution in 1:5 dilution in 0.25 N sodium hydroxide were added to the reaction medium, followed by mechanical homogenization for 15 minutes before increasing the temperature to 50° C. After 2 h45 at the temperature of 50° C., the reticulate obtained was placed in a beaker containing a phosphate buffer solution and HCl to obtain pH=7.3 and a concentration of hyaluronic acid of 25 mg/ml. The gel was left to swell for 24 h at ambient temperature in this solution, after which time it was purified by dialysis for about 24 h using cellulose dialysis membranes (retention threshold=10 000 Da) in a phosphate buffer solution until a hyaluronic acid concentration of 20 mg/ml. was obtained.

After homogenization for 15 minutes using a spatula, the oxygen contained in the gel was extracted by placing the gel in a vacuum chamber connected to a vacuum pump, and by performing 6 consecutive extraction cycles characterized by the following steps:

the vacuum chamber was placed under a dynamic vacuum at a pressure of 11 mbar for 15 minutes for the first, second and third extraction cycles, and 5 minutes for the 3 following cycles;

the vacuum was broken after each cycle by adding an adapted quantity of helium to the vacuum chamber.

The gel was then packaged in 1 ml glass syringes that were sterilized in an autoclave at 121° C. for 20 minutes. The sterilized hydrogel obtained was designated G1S.

Exactly the same preparation was carried out with the exception that:

an inert atmosphere composed of 100% nitrogen gas was used at a pressure of 1.4 bar, nitrogen replacing helium;
1.0 g of 1,4-butanedioldiglycidylether (BDDE) solution was used in a dilution of 1:5 in 0.25 N sodium hydroxide (against 1.3 g for the G1S gel).

The gel obtained was designated G2S.

Example 2: Preparation of a Crosslinked NaHA Gel According to the Prior Art (Comparative)

A laboratory mixer (air and atmospheric pressure) at ambient temperature was charged with 24 g of 0.25 N aqueous NaOH solution followed by 2.5 g of sodium hyaluronate powder (NaHA) having a molecular weight of about 1.8 MDa and moisture content of 7.8%. Hydration of the powder lasted 1 h30, with regular mechanical homogenization. 1.3 g of 1,4-butanedioldiglycidylether (BDDE) solution in 1:5 dilution in 0.25 N sodium hydroxide were added to the reaction medium followed by mechanical homogenization for 15 minutes before increasing the temperature to 50° C. After 2 h45 at the temperature of 50° C., the reticulate obtained was placed in a beaker containing a phosphate buffer solution and HCl to obtain pH=7.3 and a concentration of hyaluronic acid of 25 mg/ml. The gel was left to swell 24 h after which time it was purified by dialysis for about 24 h using cellulose dialysis membranes (retention threshold=10000 Da) in a phosphate buffer solution until a concentration of hyaluronic acid of 20 mg/ml was obtained.

After homogenization for 15 minutes using a spatula, the gel was packaged in 1 ml glass syringes that were sterilized in an autoclave at 121° C. for 20 minutes. The sterilized gel obtained was designated G3S.

Example 3: Characterization of Gels G1S, G2S and G3S by Rheology (Comparative)

The elastic moduli G' of the hydrogels G1S, G2S and G3S were measured at 0.7 Hz.

| Tested Gel | G' (0.7 Hz) in Pa (mean of 3 values measured per gel) |
|---|---|
| Gel G1S (of the invention) | 430 |
| Gel G2S (of the invention) | 342 |
| Gel G3S (of the prior art) | 333 |

It can be seen that gel G1S of the invention, prepared with exactly the same amount of crosslinker as gel G3S, has significantly higher elasticity than the latter. This imparts gel G1S with considerable benefit since it allows an increase in the capacity of the gel to push tissues and hence to create volume in vivo (a key point for the clinical efficacy of numerous crosslinked hyaluronic acid formulations in cosmetics—e.g. the case for products dedicated to restoring facial volume; and in medicine—e.g. the case for products dedicated to the treatment of incontinence).

It can also be ascertained that gel G2S of the invention prepared with a significantly lower amount of crosslinker (BDDE) than G3S, has similar/equivalent elasticity to the latter.

Therefore, in fully surprising manner, the method of the invention allows:

an improvement in the biomechanical/rheological properties of the gel, and hence an improvement in the clinical performance of the product used;
a reduction in the amount of crosslinker used (chemical agent not devoid of some toxicity) to bridge the hyaluronic acid chains, thereby improving the safety profile of the product used.

Example 4: Characterization of Gels G1S, G2S and G3S—Resistance to Degradation (Comparative)

3 transparent 30 ml jars were respectively charged with 5 ml of G1S, G2S and G3S gels. 0.5 ml of hydrogen peroxide solution (Eur. Ph.) were added to each of the 3 gels and mixed with a spatula for 5 minutes. The 3 jars were then sealed and the flow of the gels over time was observed at ambient temperature by regularly turning over each of the 3 jars simultaneously.

At t=0, it was ascertained that the 3 gels showed scarce flow and in similar manner.

After 6 h at ambient temperature, it was ascertained that the gels G2S (of the invention) and G3S flowed similarly and significantly more than gel G1S of the invention.

After 12 h at ambient temperature it was ascertained that the gels G2S (of the invention) and G3S were extremely fluid (flowed immediately as soon as they were turned over) whereas gel G1S still maintained the consistency of a viscous product (although much more fluid than at t=0).

It is inferred from this experiment that:

gel G1S of the invention, although prepared with exactly the same amount of crosslinker as gel G3S, has greater viscosity over time compared with the latter. Gels G1S and G3S both degrade over time with the solution of hydrogen peroxide, but gel G1S exhibits better resistance to degradation than G3S;

gels G2S and G3S have similar resistance to degradation with the hydrogen peroxide solution, but it is important to point out that product G2S of the invention was prepared with a significantly lower amount of crosslinker than G3S.

Therefore, in fully surprising manner, the method of the invention allows an improvement in the resistance to degradation of a crosslinked hyaluronic acid gel. This provides the developed product with a key advantage in the cosmetic or medical fields since the formulation will therefore be able to act over a longer period (improved remanence) at the injected/treated region.

Example 5: Characterization of Gels G1S, G2S and G3S—Stability Over Time (Comparative)

The elastic moduli G' of hydrogels G1S, G2S and G3S were measured at 0.7 Hz after a storage time of 12 months at ambient temperature, and the values obtained were compared with those measured at t=0.

| Tested Gel | Variation in G' (0.7 Hz) |
| --- | --- |
| Gel G1S (of the invention) | −9% |
| Gel G2S (of the invention) | −10% |
| Gel G3S (of the prior art) | −26% |

After 12 months at ambient temperature, it is ascertained that the elastic moduli G' of gels G1S and G2S of the invention show a significantly lesser decrease than gel G3S. The stability of the gels of the invention is therefore improved compared with that of the prior art gel.

Example 6: Preparation of a Crosslinked NaHA Gel of the Invention, and of a Gel According to the Prior Art (Comparative)

A laboratory mixer (air and atmospheric pressure) at ambient temperature, was charged with 19 g of 0.25 aqueous NaOH solution followed by 2.1 g of sodium hyaluronate powder (NaHA) having a molecular weight of about 1.5 MDa and moisture content of 6.1%. Hydration of the powder lasted 1 h30, with regular mechanical homogenization. 0.8 g of 1,4-butanedioldiglycidylether (BDDE) solution in 1:5 dilution in 0.25 N sodium hydroxide were added to the reaction mixture, and mechanically homogenized for 15 minutes.

Still in the laboratory mixer, an oxygen extraction step was performed (total duration of the step=8 minutes) to extract the oxygen contained in the reaction mixture by performing 1 extraction cycle characterized as follows:

the mixture chamber was placed under a dynamic vacuum at a pressure of 52 mbar for 6 minutes;

the vacuum was broken by adding an adapted quantity of nitrogen to the mixer chamber.

The temperature inside the mixer chamber was brought to 50° C. for 3 h00 to crosslink the reaction mixture in an inert atmosphere composed of 100% nitrogen gas at a pressure of 1.9 bar. After this time, the reticulate obtained was placed in a beaker containing a phosphate buffer solution and HCl to obtain pH=7.3 and a concentration of hyaluronic acid of 25 mg/ml. The gel was left to swell for 24 h at ambient temperature in this solution and then purified by dialysis for about 24 h using cellulose dialysis membranes (retention threshold=10000 Da) in a phosphate buffer solution until a hyaluronic acid concentration of 20 mg/ml was obtained.

After homogenization for 15 minutes using a spatula, the oxygen contained in the gel was extracted by placing the gel in a vacuum chamber connected to a vacuum pump and by performing 4 consecutive extraction cycles characterized by the following steps:

the vacuum chamber was placed under a dynamic vacuum at a pressure of 20 mbar for 10 minutes for the first, second and third extraction cycles, and for 5 minutes for the fourth cycle;

the vacuum was broken by adding an adapted quantity of nitrogen to the vacuum chamber.

The gel was then packaged in 1 ml glass syringes that were sterilized in an autoclave at 121° C. for 20 minutes. The sterilized hydrogel obtained (of the invention) was designated G4S.

Exactly the same preparation was carried out with the exception that:

0.9 g of 1,4-butanedioldiglycidylether (BDDE) solution in 1:5 dilution in 0.25 N sodium hydroxide were added to the reaction medium (instead of 0.8 g for gel G4S)

the medium was left to stand 8 minutes after adding BDDE and mechanically homogenized for 15 minutes, instead of the step to extract the oxygen contained in the reaction medium;

crosslinking was performed in air (i.e. not in an inert atmosphere);

no oxygen extraction step was performed after purification of the gel by dialysis or before packaging in syringes.

The sterilized (prior art) gel obtained was designated G5S.

The elastic moduli G' of hydrogels G4S and G5S were measured at 0.7 Hz.

| Tested Gel | G' (0.7 Hz) in Pa (mean of 3 values measured per gel) |
| --- | --- |
| Gel G4S (of the invention) | 393 |
| Gel G5S (of the prior art) | 317 |

As shown in Example 3, it is confirmed in this new example that the preparation method of the invention has strong action on the structure of a crosslinked hyaluronic acid hydrogel.

Although a greater quantity of crosslinking agent was used (over 10% more BDDE) to prepare the prior art gel G5S, it is ascertained that this product is less crosslinked and less robust than gel G4S of the invention (the value of G' at 0.7 Hz is lower than that of gel G4S).

This example therefore provides confirmation that, in fully surprising manner, the method of the invention allows:
- an improvement in the biomechanical/rheological properties of the gel, and hence an improvement in the clinical performance of the product used;
- a reduction in the amount of crosslinker (chemical agent not devoid of some toxicity) added to the reaction mixture to crosslink the hyaluronic acid chains, thereby improving the safety profile of the product used.

The invention claimed is:

1. A method for preparing an injectable hydrogel of crosslinked hyaluronic acid, or one of the salts thereof, and optionally the injectable hydrogel further comprising other biocompatible polymers, the method comprising at least the following steps:
   preparing a hydrogel by integrating at least one crosslinking step of the hyaluronic acid in an aqueous solution, wherein the at least one cross-linking step is performed in an inert atmosphere;
   leaving the formed hydrogel to swell in said aqueous solution;
   purifying the hydrogel;
   packaging the hydrogel in syringes or bottles; and
   sterilizing the packaged hydrogel;
wherein the method further comprises performing mandatorily at least one extraction step of the oxygen contained in the hydrogel, the extraction step being performed after the crosslinking step of the hyaluronic acid in the inert atmosphere and purification of said hydrogel and before and/or at the time of packaging the hydrogel; the extraction step comprising performing at least one extraction cycle in a suitable container, the extraction cycle comprising the following successive steps:
   placing the container containing the hydrogel under a vacuum at a pressure (p) lower than atmospheric pressure for a time (t); and
   breaking the vacuum after time (t) by adding an adapted quantity of a gas other than oxygen, wherein variation of the elastic moduli G' of the hydrogel is less than or equal to 10% when measured at 0.7 Hz after a storage time of 12 months at ambient temperature.

2. The method according to claim 1, wherein the inert atmosphere used comprises one or more medical grade gases.

3. The method according to claim 1, wherein the inert atmosphere comprises one or more of the following gases: hydrogen, helium, nitrogen and argon.

4. The method according to claim 1, wherein the inert atmosphere is at a pressure equal to or higher than atmospheric pressure.

5. The method according to claim 1, wherein, for the oxygen extraction step, the step of placing the container containing the hydrogel under the vacuum takes place in a vacuum chamber.

6. The method according to claim 1, wherein, for the oxygen extraction step, the step of placing the container containing the hydrogel under the vacuum is performed at a pressure lower than 100 mbar, or lower than 50 mbar.

7. The method according to claim 1, wherein, for the oxygen extraction step, the step of placing the container containing the hydrogel under the vacuum is performed dynamically.

8. The method according to claim 1, wherein, for the oxygen extraction step, the vacuum is applied for between 1 minute and 60 minutes, or between 5 minutes and 25 minutes.

9. The method according to claim 1, wherein, for the oxygen extraction step, the gas other than oxygen is an inert gas or a mixture of inert gases.

10. The method according to claim 1, wherein, for the oxygen extraction step, the gas other than oxygen is selected from the group consisting of hydrogen, helium, nitrogen and argon.

11. The method according to claim 1, wherein, for the oxygen extraction step, the gas other than oxygen is a medical grade gas.

12. The method according to claim 1, wherein, for the oxygen extraction step, extraction cycles to extract the oxygen contained in the hydrogel after the crosslinking step are performed between 1 and 4 times.

13. The method according to claim 1, wherein, for the oxygen extraction step, each oxygen extraction step performed in the production of the hydrogel comprises a number of extraction cycles between 1 and 50, between 2 and 10, or between 3 and 6.

14. The method according to claim 1, wherein, before the crosslinking step of the hyaluronic acid in an inert atmosphere, a further step to extract the oxygen contained in the aqueous solution is performed.

15. A sterile injectable hydrogel containing crosslinked hyaluronic acid obtained according to claim 1.

16. A method of treating a subject comprising administering a sterile injectable hydrogel according to claim 15 to said subject.

* * * * *